United States Patent
Lee

(10) Patent No.: US 6,383,797 B1
(45) Date of Patent: May 7, 2002

(54) BACTERIAL CONSORTIUM EBC1000 AND A METHOD USING THE BACTERIAL CONSORTIUM EBC1000 FOR REMEDYING BIOLOGICALLY RECALCITRANT TOXIC CHEMICALS CONTAINED IN INDUSTRIAL WASTEWATER, WASTE MATERIALS AND SOILS

(76) Inventor: Sung-gie Lee, 106-304, Geonyoung-Apartment, 2099, Yongam-Dong, Sangdang-Ku, 360-181 Cheongjoo-Si, Choongchung-Book-Do (KR)

( * ) Notice: Subject to any disclaimer, the term of this patent is extended or adjusted under 35 U.S.C. 154(b) by 0 days.

(21) Appl. No.: 09/787,872

(22) PCT Filed: Jul. 22, 2000

(86) PCT No.: PCT/KR00/00747

§ 371 Date: Mar. 23, 2001

§ 102(e) Date: Mar. 23, 2001

(87) PCT Pub. No.: WO01/14526

PCT Pub. Date: Mar. 1, 2001

(30) Foreign Application Priority Data

Aug. 20, 1999 (KR) ........................................ 1999-34664

(51) Int. Cl.[7] ................................................. C12N 1/20
(52) U.S. Cl. ................. 435/252.4; 435/262; 435/262.5; 210/605; 210/610; 210/611; 210/620; 210/630
(58) Field of Search .............................. 435/252.4, 262, 435/262.5; 210/605, 610, 611, 620, 630

(56) References Cited

U.S. PATENT DOCUMENTS 5,705,072 A * 1/1998 Haase ......................... 210/605

FOREIGN PATENT DOCUMENTS

WO    WO-94/29227    * 12/1994

* cited by examiner

*Primary Examiner*—Francisco Prats
*Assistant Examiner*—Kailash C. Srivastava
(74) *Attorney, Agent, or Firm*—Browdy and Neimark, P.L.L.C.

(57) ABSTRACT

The present invention relates to a novel bacterial consortium EBC1000 (KCTC 0652 BP) and a method for remedying biologically a chlorine compound and recalcitrant toxic chemicals contained in industrial wastewater, waste materials and soils using the bacterial consortium EBC1000. The novel bacterial consortium EBC1000(KCTC 0652 BP) is composed of aerobic bacterium easy to culture and useful for decomposing a chlorine compound and waste acidic or alkaline recalcitrant toxic chemicals of high concentration contained in the industrial waste materials, such as IPA, MC, DMA, AN, SHS, BD, Tamol-SN, EDTA, FES, TDDM, PMH, DEHA, MeOH, NaOH and $CH_3CN$, thus preventing and recovering environmental pollutions.

14 Claims, No Drawings ized from soil and wastewater having $COD_{Mn}$ of 20,000 to
BACTERIAL CONSORTIUM EBC1000 AND A METHOD USING THE BACTERIAL CONSORTIUM EBC1000 FOR REMEDYING BIOLOGICALLY RECALCITRANT TOXIC CHEMICALS CONTAINED IN INDUSTRIAL WASTEWATER, WASTE MATERIALS AND SOILS

REFERENCE TO RELATED APPLICATIONS

The present application is the national stage under 35 U.S.C. 371 of international application PCT/KR00/00747, filed Jul. 22, 2000 which designated the United States, and which international application was published under PCT Article 21(2) in the English language.

FIELD OF THE INVENTION

The present invention relates to a novel bacterial consortium EBC1000 and a method for remedying biologically recalcitrant toxic chemicals contained in industrial wastewater, waste materials and soils using the bacterial consortium EBC1000. More particularly, the invention relates to a novel bacterial consortium EBC1000 capable of remarkably decomposing a chlorine compound of high concentration and waste acidic or alkaline recalcitrant toxic chemicals difficult to be degraded that are isolated from waste soil and water, the recalcitrant toxic chemicals having a chemical oxygen demand ($COD_{Mn}$) of 20,000 to 100,000 ppm and comprising chemicals, such as isopropyl alcohol (IPA), methylene chloride (MC), dimethylamine (DMA), acrylonitrile (AN), hydrosulfite (SHS), butadiene (BD), sodium alkylaryl naphthalene sulfonate (Tamol-SN), tetra sodium ethylene diamine tetra acetate dihydrate (EDTA), ferrous sulfate heptahydrate (FES), tert-dodecyl mercaptan (TDDM), paramethane hydroperoxide (PMH), N-diethyl hydroxyl amine (DEHA), methanol (MeOH), NaOH and $CH_3CN$.

BACKGROUND ART

Environmental contaminations, which are caused by recalcitrant toxic substances, often lead to (i) degradation of food stuffs for humans related to the food chain in the biosphere, (ii) prevalence of infection diseases due to deteriorated immunity, and (iii) spread of chronic diseases and energy exhaustion. Once the ecosphere is radically destroyed, it may take several hundred millions of years for the environment of the ecosphere to recover. degradation of food stuffs for human related to the food chain in the biosphere, prevalence of infectious diseases due to deteriorated immunity, spread of chronic diseases and energy exhaustion. Once the ecosphere is radically destroyed, it may take several hundred millions of years for recovery of the environment of ecosphere.

There has been an attempt to remedy recalcitrant toxic substances contained in the industrial wastewater or noxious waste materials dumped into the sea normally, using physical and chemical methods such as incineration, landfill, chemicals, electrolysis, membrane separation or the like. However, these conventional methods also involve economical and environmental problems. The most efficient and safe method that meets requirements in every aspect of environmentology, sanitation, ecology and economy is the biological treatment method. Many studies have been made on the biological methods, for example, using the natural ecosystem such as silt at an estuary. However, these methods could not be a solution of treating a great mass of industrial waste materials.

DISCLOSURE OF THE INVENTION

It is, therefore, an object of the present invention to provide bioremediation to remedy biologically recalcitrant toxic chemicals contaminating industrial wastewater, waste materials and soils, etc., using a trace of useful specific bacterial consortium that exists in the ecological system.

The present invention is directed to a novel bacterial consortium EBC1000 and a method for remedying biologically recalcitrant toxic chemicals and chlorine compounds contained in industrial wastewater, waste materials, soils, or the like using the bacterial consortium EBC1000. More particularly, the invention is directed to a novel bacterial consortium EBC1000 capable of remarkably degrading chlorine compounds of high concentration and waste acidic or waste alkaline recalcitrant toxic chemicals that are isolated from soil and wastewater having $COD_{Mn}$ of 20,000 to 100,000 ppm, such as contained in the medical industrial wastewater to be dumped into the sea, e.g., isopropyl alcohol, methylene chloride, NaOH, $Na_2SO_4$, dimethylamine or methanol, or as contained in the petroleum industrial wastewater to be dumped into the sea, e.g., sodium hydrosulfite, butadiene, sodium alkylaryl naphthalene sulfonate, acrylonitrile, tetra sodium ethylene diamine tetra acetate dihydrate, ferrous sulfate heptahydrate, tert-dodecyl mercaptan, paramethane hydroperoxide, N-diethyl hydroxy amine, and $CH_3CN$.

The inventor isolated a novel bacterial consortium EBC1000 (KCTC 0652 BP) having a characteristic of rapidly degrading recalcitrant waste materials of high concentration dumped into the sea as well as chlorine compounds, from the soils and wastewater collected from the Ulsan industrial complex and the petroleum chemical industrial complex in Korea. The bacterial consortium EBC1000 consists of nine strains, each having the ability of degrading recalcitrant waste materials. It was found that the bacterial consortium EBC1000 degrades waste acidic or waste alkaline recalcitrant waste materials having the $COD_{Mn}$ of 20,000 to 100,000 ppm contained in the medical and petroleum industrial wastewaters to be dumped into the sea by 80% within 7 days, 90% within 10 days and at least 80 to 90% within 240 hours in an aerobic manner. Examples of the waste acidic or alkaline recalcitrant waste materials contained in the medical industrial wastewater of e.g., pH 3 or 14 include isopropyl alcohol (IPA, 10,000 to 20,000 ppm), methylene chloride (MC, 100 to 7,000 ppm), NaOH (changeable), $Na_2SO_4$ (changeable), dimethylamine (DMA, 70 to 2,500 ppm), methanol (MeOH, 27,000 to 54,000 ppm), organic matters and antibiotic residues (40,000 to 100,000 ppm) and $Cl^-$ (4,000 to 33,000 ppm). Examples of the waste acidic or alkaline recalcitrant waste materials contained in the petroleum industrial wastewater of e.g., pH 1.2, 3.0 or 5.0 include sodium hydrosulfite (SHS, $(NaSO_2)_2$, 30 ppm), butadiene (BD,changeable), sodium alkylaryl naphthalene sulfonate (Tamol-SN, 4,000 to 20,000 ppm), acrylonitrile (AN,changeable), tetra sodium ethylene diamine tetra acetate dihydrate (EDTA, 20 to 200 ppm), ferrous sulfate heptahydrate (FES, 60 ppm), tert-dodecyl mercaptan (TDDM, 4,000 ppm), paramethane hydroperoxide (PMH, 400 ppm), N-diethyl hydroxyl amine (DEHA, 200 ppm), and $CH_3CN$ (changeable).

Accordingly, the present invention is to provide such a novel bacterial consortium EBC1000 capable of degrading recalcitrant toxic chemicals and chlorine compounds, and a method using the bacterial consortium EBC1000 in remedying biologically recalcitrant toxic chemicals and chlorine compounds contaminating industrial wastewater, waste materials and soils.

BEST MODE FOR CARRYING OUT THE INVENTION

Now, a description will be made to isolation, identification and activity of the novel bacterial consortium EBC1000.

1. Isolation of Novel Bacterial Consortium EBC1000

(1) Isolation of 40 Strains from Shaking Culture of the Samples

The soil (1 g) and wastewater (10 ml) from the Ulsan industrial complex were inoculated in a waste acidic and alkaline waste liquid medium (prepared by dilution of $K_2HPO_4$ (0.65 g), $KH_2PO_4$ (0.17 g), $MgSO_4$ (0.1 g), $NaNO_3$ (0.5 g) and 10% waste acidic and alkaline wastewater containing recalcitrant chemicals in medical and petroleum industrial waste liquid, in 1 liter of deionized water, pH 0 to 14) and then in a chlorine compound liquid medium (prepared by dissolving of $K_2HPO_4$ (0.65 g), $KH_2PO_4$ (0.17 g), $MgSO_4$ (0.1 g), $NaNO_3$ (0.5 g) and pentachlorophenol (PCP, 50 ppm) in 1 liter of deionized water, pH 7.2), followed by shaking culture at 20 to 30° C. for more than 5 days.

1 ml of the shaken culture was collected and inoculated in a waste acidic or waste alkaline solid medium (prepared by adding only 1.5% of agar to the waste acidic or alkaline liquid culture, pH 7.0) and then a chlorine compound solid medium (prepared by adding 20 mg of BTB and 1.5% of agar to the chlorine compound liquid medium), followed by incubation at 20 to 30° C. for 3 to 10 days.

The individual pure colonies isolated were further inoculated in the above mentioned cultures and then cultured with shaking, thus isolating 40 useful bacterial strains which have a different colony form formed respectively and the same colony after successive transfer culture.

(2) Isolation of 9 Component Strains After the Bacteria Isolated in Step (1) are cultured in the Medium of an Increased Concentration of the Recalcitrant Wastewater The bacteria isolated in step (1) were in order and individually inoculated in a minimal medium containing 50% of the crude wastewater and 80% of wastewater containing the recalcitrant chemicals of the medical and petroleum wastewater and then a minimal medium containing 500 ppm of the pentachlorophenol compound and subjected to the same procedures of step (1), thus isolating nine competent strains viable in the wastewater of higher concentration of the recalcitrant chemicals.

The nine bacterial strains, which constitute a single bacterial consortium, named "EBC1000", are designated as EBC100, EBC101, EBC103, EBC104, EBC105, EBC106, EBC107, EBC108 and EBC109.

The novel bacterial consortium EBC1000 was deposited in the Korean Collection for Type Cultures in the Korea Research Institute of Bioscience and Biotechnology as the deposition No. KCTC 0652 BP on Aug. 12, 1999.

2. Optimum Conditions for Growth of Bacterial Consortium EBC1000

The bacterial consortium EBC1000 had the best growth in the Luria-Bertani nutrient medium (containing 10 g of bacto-tryptone, 5 g of bacto-yeast extract and 10 g of NaCl in 1 liter of deionized water) at pH 5 to 8 and 25 to 35° C. with shaking at 50 to 100 rpm/min for 24 to 48 hours. The bacterial consortium EBC1000 was also well grown in the successive transfer culture under the same conditions.

3. Identification of Bacterial Consortium EBC1000

The individual strains constituting the bacterial consortium EBC1000, designated as EBC100, EBC101, EBC103, EBC104, EBC105, EBC106, EBC107, EBC108 and EBC109 are a mixture of Gram negative and positive bacteria and have unique shape and size. After culture for 24 hours in the Luria-Bertani medium, EBC100 forms a 1mm-diameter circular colony, EBC101 a large about 2 mm-diameter circular colony, EBC103 a thick about 2 mm-diameter circular colony, EBC104 and EBC105 a small about 0.5 mm-diameter circular colony, EBC106 a thick about 3 mm-diameter colony, EBC107 a about 1.2 mm-diameter brownish colony, EBC108 a about 1 mm-diameter yellowish colony, and EBC109 a about 2-diameter double circle. These nine strains are aerobic and air permeable bacteria. EBC100, EBC101, EBC103, EBC106, EBC107 and EBC108 have high viability in the strong acidic condition of pH 3 to 4 and in the strong alkaline condition of pH 9 to 11. EBC104, EBC105 and EBC109 are slow in growth and EBC100, EBC104, EBC105 and EBC109 show mobility.

For the genera of the individual constituent strains of the bacterial consortium EBC1000 included EBC100, EBC101 and EBC103 are the strains of the genus Klebsiella, EBC105 Providencia, EBC104 and EBC109 Escherichia, EBC106 Bacillus, EBC107 Gram-negative bacteria and EBC108 Gram-positive Bacteria.

The characteristics of the individual strains are presented in Tables 1 and 2.

| Characteristic | EBC 100 | EBC 101 | EBC 103 |
|---|---|---|---|
| Gram Stain | − | − | − |
| Catalase | + | | |
| Oxidase | − | | |
| Urease | + | | |
| Citrase Utilization | + | | |
| Glucose Utilization | + | | |
| V-P Test | + | | |
| Lysine Decarboxylase | + | | |
| Ornithine Decarboxylase | − | | |

TABLE 1b

| Characteristic | EBC 100 | EBC 101 | EBC 103 |
|---|---|---|---|
| Inositol | + | | + |
| Arabinose | + | + | + |
| Mannitol | + | + | + |
| Rhamnose | + | + | + |
| Glucose | + | + | + |
| Sorbitol | + | + | + |
| α-cyclodextrin | − | − | − |
| Dextrin | + | + | − |
| Glycogen | | | − |
| Adonitol | + | + | |
| D-Arabitol | | + | + |
| Cellobiose | | + | + |
| D-Fructose | + | + | + |
| L-Fucose | + | + | + |
| D-Galactose | + | + | + |
| α-Lactose | | | − |
| Maltose | | + | + |
| D-Raffinose | | + | + |
| D-Trehalose | + | + | + |
| Methyl-pyruvate | − | + | + |
| Citric Acid | + | + | + |
| Formic Acid | | | + |
| Malonic Acid | − | − | |
| Succinic Acid | | | + |
| D-Alanine | | | + |
| L-Alanine | + | | + |
| L-Glutamic Acid | | + | + |

TABLE 1b-continued

| Characteristic | EBC 100 | EBC 101 | EBC 103 |
|---|---|---|---|
| L-Serine | + | + | + |
| D,L-Lactic Acid | + | + | + |
| Mobility | + | + | + |
| D-Mannose | + | + | + |

| Characteristic | EBC 104 | EBC 105 | EBC 109 |
|---|---|---|---|
| Gram Stain | − | − | − |
| ONPG | + | − | + |
| Arginine | − | − | − |
| Lysine | + | − | − |
| Ornithine | − | − | − |
| Sodium Citrate | − | − | − |
| Sodium Thiosulfate | + | − | + |
| Urea | − | + | − |
| Tryptophane | − | + | − |
| Indole | + | + | + |
| Sodium Pyruvate Creatine | − | − | − |
| Kohn Charcoal Gelatin | − | − | − |
| Glucose Potassium Nitrate | + | + | + |
| Mannitol | − | − | − |
| Inositol | + | − | + |
| Rhamnose | + | + | + |
| Sucrose | − | − | − |
| Melibiose | − | − | − |
| Amygdalin | − | − | − |
| Arabinose | + | − | + |
| Oxidase | − | − | − |
| Reduction of Nitrates to Nitrates | + | + | + |
| Reduction of Nitrates to $N_2$ gas | − | − | − |
| Mobility | + | + | + |
| Oxidation of Glucose | + | + | + |
| Fermentation of Glucose | + | − | + |
| Antibiotic Resistance | $Km^R$ $Ap^S$ $Tc^S$ | $Km^S$ $Ap^R$ $Tc^R$ | $Km^S$ $Ap^R$ $Tc^R$ |

On the other hand, the individual bacterial strains were analyzed for fatty acid Methyl Esters (FAMEs) by gas chromatography.

For the FAMEs assay, there was used the Hewlett Packard series II Gas Chromatograph model 5890A (Microbial ID. Inc., Delaware, USA) with a 25 cm×0.22 mm×0.33 μm separation column, e.g., a capillary column (HP 19091B-102) fused with methylphenyl silicon.

The gas chromatography was performed under the conditions that the carrier gas is hydrogen, the column head pressure 10 psi, the split ratio 100:1, the split vent 50 ml/min, the septum purge 5 ml/min, the FID hydrogen flux 30 ml/min, the FID nitrogen flux 30 ml/min, the FID air 400 ml/min, the initial temperature 170° C., the program rate 5° C./min, the final temperature 270° C., the FID temperature 300° C., the temperature of the inlet port 250° C., and the injection volume 2 μl.

The FAME graphs were obtained using a microbial identification system software (Microbial ID, Inc., Delaware, USA). A comparison with a standard calibration mixture (Microbial ID. Inc., Delaware, USA) enabled peak identification, and determination of retention time, peak region and peak percentage.

The assay of the FAMEs for the respective strains of EBC100, 101 and 103 revealed that the intracellular fatty acids composition is C12:0, C14:0, C16:0, C16:1, C17:0 cyclo and C14:0 3OH for EBC100; C12:0, C14:0, C15:0, C16:0, C17:0 cyclo and C14:0 3OH for EBC101; and C14:0, C15:0, C16:0, C17:0 cyclo, and C14:0 3OH for EBC103.

4. Isolation of Constituent Strains of Bacterial Consortium EBC1000

The following procedures are performed for isolating the individual strains from the bacterial consortium EBC1000.

When cultured in the Luria-Bertani agar solid nutrient medium (containing 10 g of bacto-tryptone, 5 g of bacto-yeast extract, 10 g of NaCl and 1.5% agar in 950 ml of deionized water), EBC106 (Bacillus) is characterized by a thick wrinkle peculiar to the Bacillus, EBC107 (Gram negative bacteria) a brownish colony, and EBC108 (Gram positive bacteria) a yellowish colony.

For the other strains the respective colonies can be identified by dilution-smearing the bacterial consortium EBC1000 in desoxycholate agar containing 10 g of bacto-peptone, 10 g of bacto-lactose, 1 g of sodium desoxycholate, 5 g of sodium chloride, 2 g of dipotassium, 1 g of ferrous citrate, 1 g of sodium citrate, 15 g of bacto agar and 0.03 g of neutral red in 1 liter of deionized water (Difco manual, 1984). After cultured for 24 hours in the desoxycholate agar, EBC100, EBC101 and EBC103 have white-in-red spots with viscosity and are slightly different in size, EBC104 white-in-red spots without viscosity, EBC105 brownish spots with viscosity, EBC106 and EBC107 light brownish spots with viscosity, EBC108 colorless spots with viscosity, and EBC109 red spots with viscosity (See. Dictionary of Microbiology and Molecular Biology, $2^{nd}$, Paul Singleton Diana Sainsbury, 1987).

5. Characteristics of Bacterial Consortium EBC1000

(1) Decomposition Velocity of sodium Alkylaryl naphthalene sulfonate (Tamol-SN) by Bacterial Consortium EBC1000

Batches of Tamol-SN with an increasing concentration of 500 ppm, 1000 ppm, 2000 ppm and 4000 ppm were added to the minimal medium (pH 7.2) prepared by dissolving 0.065 g of $K_2HPO_4$, 0.017 g of $KH_2PO_4$, 0.1 g of $MgSO_4$ and 0.5 g of $NaNO_3$ in 1 liter of deionized water. After inoculation of the bacterial consortium EBC1000, the absorbance and the Tamol-SN concentration were measured with an elapse of time. The results are presented in Table 3.

TABLE 3

| Tamol-SN (ppm) | Decomposition Velocity (mg/l/h) |
|---|---|
| 500 | 1.3 |
| 1000 | 3.8 |
| 2000 | 5.2 |
| 4000 | 4.0 |

As shown in Table 3, the decomposition velocity per hour of Tamol-SN was 1.3 mg/l/h at the Tamol-SN concentration of 500 ppm and 4.0 mg/l/h at the Tamol-SN concentration of 4000 pm.

(2) Decomposition Velocity of pentachlorophenol Compound by bacterial Consortium EBC1000

Batches of pentachlorophenol compound with an increasing concentration of 200 ppm, 500 ppm, 1000 ppm and 2000 ppm were added to the medium prepared by dissolving 20 mg of BTB in 1 liter of deionized water under the same conditions of the minimal liquid medium as described in (1). After inoculation of the bacterial consortium EBC1000, the absorbance and the pentachlorophenol compound concentration per hour were measured. The results are presented in Table 4.

TABLE 4

| Pentachlorophenol Compound (ppm) | Decomposition Velocity (mg/l/h) |
| --- | --- |
| 200 | 0.9 |
| 500 | 6.5 |
| 1000 | 5.0 |
| 2000 | 4.5 |

6. Treatment of Recalcitrant Industrial Wastewater with Bacterial Consortium EBC1000

EXPERIMENTAL EXAMPLE 1

Use of Bacterial Consortium EBC1000 in Treatment of a Recalcitrant Special Emulsifying agent Contained in Petroleum Industrial Wastewater 1% of crude liquid of sodium alkylaryl naphthalene sulfonate (Tamol-SN), which is the typical recalcitrant chemical used in the petroleum plant, was added to 50 ml of a minimal medium (pH 7.2) prepared by dissolving 0.065 g of $K_2HPO_4$, 0.017 g of $KH_2PO_4$, 0.1 g of $MgSO_4$ and 0.5 g of $NaNO_3$ in 1 liter of deionized water. After inoculating $2.0 \times 10^4$/ml of the bacterial consortium EBC1000, shaking culture was performed at 100 rpm, at 25 to 30° C. for 10 days. The results are presented in Table 5.

TABLE 5

| Time (day) | Tamol-SN (ppm) | Number of Bacterium (CFU/ml) |
| --- | --- | --- |
| 0 | 10000 | $2.0 \times 10^4$ |
| 2 | 6000 | $3.5 \times 10^5$ |
| 3 | 3600 | $3.0 \times 10^6$ |
| 4 | 850 | $2.5 \times 10^7$ |
| 10 | 500 | $3.0 \times 10^7$ |

As shown Table 5, the concentration of Tamol-SN was 850 ppm with the number of bacteria of $2.5 \times 10^7$ CFU/ml after four days of culture.

EXPERIMENTAL EXAMPLE 2

Use of Bacterial Consortium EBC1000 in Treatment of Recalcitrant Crude Wastewater from Petroleum Plants Waste acidic and alkaline recalcitrant wastewater to be dumped into the sea was collected from the petroleum plants in the Ulsan industrial complex. The wastewater was crude wastewater contained 4000 ppm of sodium alkylaryl naphthalene sulfanate (Tamol-SN), sodium hydrosulfite[$(NaSO_2)_2$], butadiene (BD), acrylonitrile (AN), tetra sodium ethylene diamine tetra acetate dihydrate (EDTA), ferrous sulfate heptahydrate (FES), tert-dodecyl mercaptan (TDDM), paramethane hydroperoxide (PMH), N-diethyl hydroxy amine (DEHA) and $CH_3CN$ and so on. After inoculating $1.2 \times 10^7$/ml of EBC1000 in 200 ml of the crude wastewater, shaking culture was performed at 80 rpm, at 30° C. for 10 days. The results are presented in Table 6.

| Time (day) | $COD_{Mn}$ (ppm) | TOC (ppm) | BOD (ppm) | Number of Bacteria |
| --- | --- | --- | --- | --- |
| 0 | 4000 | 3348 | 610 | $1.2 \times 10^7$ |
| 4 | 1882 | 1670 | — | $4.0 \times 10^9$ |
| 6 | 1136 | 1220 | 400 | $4.8 \times 10^9$ |
| 10 | 750 | 980 | 200 | $5.1 \times 10^9$ |

As shown in Table 6, the COD value of the crude wastewater was reduced to 750 ppm with the decomposition efficiency of 80% after 10 days of culture. The TOC and BOD values had a downward tendency as the COD value and the number of bacteria was $5.1 \times 10^9$ CFU/ml with an at least hundred-fold increase.

For a reference, the analytical methods used in the experimental examples of the present invention were as follows:

1) COD (Mn) Analysis

The chemical oxygen demand (COD) was measured by the COD Mn method according to the official test method for water pollution and waste treatment (Official No. 1993-42, the Ministry of Environment) and Standard Methods (APHA, AWWA, WPCF, $18^{th}$ ed.). Each 10 ml of crude industrial wastewater or waste materials to be dumped into the sea and the wastewater after decomposition treatment of noxious substances with microorganisms were added to a water bath after addition of $H_2SO_4$ and 0.025N $KMnO_4$, and then heated to 100° C. for 30 minutes. After adding 0.025N $Na_2C_2O_4$, the mixture was titrated with $KMnO_4$ to measure the actual decrement of the COD.

2) BOD Analysis

The biological oxygen demand (BOD) was measured as the amount of dissolved oxygen used for 5 days under the biological reaction at 20° C. according to the official test method for water pollution and waste treatment and Standard Methods.

3) TOC Analysis

According to the standard method, the crude waste, wastewater and the time-based samples were centrifuged and the resulting supernatant liquids were analyzed for the total organic carbon (TOC) content with a TOC analyzer (TOC-5000 A, Shimadzu com.).

4) CFU Examination

The consortiums of indigenous bacteria and inocula of the individual treated samples were analyzed by the plate count method according to the standard method for bacterial examination, to measure the growth of the bacteria at the beginning of the test and with an elapse of time by a decrease in the noxious substances.

5) Extraction and Analysis of Chlorine Compound

The chlorine compound was extracted and analyzed according to the contents of Korean Patent No. 154295 or Korean Patent Application No. 98-20706, and a paper by the inventor (Journal of Applied Microbiology 85-1-1~8, 1998; Journal of Korea Soil Environment Society, 1-1-39~46, 1996).

EXPERIMENTAL EXAMPLE 3

Use of Bacterial Consortium EBC1000 in Treatment of Recalcitrant Wastewater from Medicine Manufacturing Plant Waste acidic and alkaline recalcitrant wastewater to be dumped into the sea was collected from the medicine manufacturing plants in the Ulsan industrial complex and the middle north region. The waste materials contained medical residues and isopropyl alcohol (IPA), methylene chloride (MC), NaOH, $Na_2SO_4$, dimethylamine (DMA) and methanol and exhibited a high $COD_{Mn}$ value of 20,000 to 100,000 ppm. After inoculating $2.0\times10^7$/ml of EBC1000 in each 200 ml of the wastewater, culture was performed with aeration at 20 to 25° C. for 14 days. The results are presented in Table 7.

standed for one day and added to a slurry apparatus. Compared to decomposition efficiency of the pentachlorophenol compound by the Bu34 strain+11 decomposition strains (a deposited strain Bu1 presented in Korean Patent Application No. 98-20706 and 10 unidentified strains decomposing pentachlorophenol)+an unidentified indigenous strain (which appeared in a control apart from the decomposition strains and was isolated by a relative comparison in regard to the distribution of the indigenous strain), the novel bacterial consortium EBC1000 showed a slightly higher decomposition efficiency, as seen in Table 8. For example, after 14 days, the decomposition efficiency for removal of the chlorine compound was 96% for the Bu34 strain but 98% for the novel bacterial consortium EBC1000.

TABLE 8

| Time (day) | Bu34 + 11 Dec. Strains + Indigenous Strain | | EBC 1000 | |
| --- | --- | --- | --- | --- |
| | Absorbance (A660) | PCP (ppm) | Absorbance (A660) | PCP (ppm) |
| 0 | 0.400 | 250 | 0.350 | 250 |
| 2 | 0.699 | 113 | 0.900 | 100 |
| 5 | 0.710 | 75 | 1.180 | 60 |
| 8 | 0.947 | 50 | 1.200 | 35 |
| 10 | 1.050 | 38 | 1.500 | 20 |
| 14 | 1.164 | 10 | 1.560 | 5 |

| Time (day) | $COD_{Mn}$ (ppm) | TOC (ppm) | BOD (ppm) | Number of Bacteria (CFU/ml) |
| --- | --- | --- | --- | --- |
| 0 | 3800 | 34000 | 34500 | $2.0 \times 10^7$ |
| 3 | 12000 | 21000 | — | $3.4 \times 10^7$ |
| 5 | 10800 | 14600 | — | $2.0 \times 10^9$ |
| 7 | 8300 | 10200 | — | $1.4 \times 10^{11}$ |
| 10 | 4000 | 7200 | — | $1.6 \times 10^{10}$ |
| 14 | 3300 | 4300 | 4080 | $3.6 \times 10^{10}$ |

EXPERIMENTAL EXAMPLE 5

After 5 g each of chip and sawdust from waste timber was added to 65 ml of the minimal liquid medium, EBC1000 was, subjected to shaking culture at 90 to 100 rpm and 30° C. for 90 hours. The results are presented in Table 9. As shown in Table 9, after 80 hours, the decomposition efficiency of pentachlorophenol (PCP) was 98% under inoculation of EBC1000 with a hundred-fold increase in the number of bacteria.

| | Chip or Sawdust (Bu1 + Bu34) | | Chip or Sawdust (EBC 1000) | |
| --- | --- | --- | --- | --- |
| Time (hour) | PCP (µg/g, dry) | Number of Bacteria (CFU/ml) | PCP (µg/g, dry) | Number of Bacteria (CFU/ml) |
| 0 | 1080 | $1.4 \times 10^7$ | 1080 | $2.5 \times 10^7$ |
| 48 | — | — | 460 | $7.9 \times 10^8$ |
| 80 | — | — | 26 | $3.0 \times 10^9$ |
| 90 | 27 | $5.0 \times 10^8$ | 20 | $3.1 \times 10^9$ |

As shown in Table 7, the COD value of the crude wastewater was reduced to 4000 ppm with the decomposition efficiency of 90% after 10 days of culture. The TOC and BOD values also had a downward tendency as the COD value and the number of bacteria of EBC1000 was $1.6\times10^{10}$ CFU/ml with an at least ten hundred-fold increase.

7. Tests for Soil and Timber Contaminated by Chlorine Compound

EXPERIMENTAL EXAMPLE 4

Use of Bacterial Consortium EBC1000 in Treatment of Soil Contaminated by Chlorine Compound 600 g of the soil contaminated by the pentachlorophenol compound (PCP) was dispersed in 5 liters of tap water

EXPERIMENTAL EXAMPLE 6

200 g of sawdust from waste timber was added to 250 ml of the minimal liquid medium, followed by adding EBC1000 of $2.0\times10^8$/g (timber). Then, moisture and strains were added to the sawdust and the mixture was allowed to stand at room temperature for 200 days (See. "Composing Method", McBain et al., Biodegradation 6, 47–55, 1995). The results are presented in Table 10. As shown in Table 10, the novel bacterial consortium EBC1000 showed higher decomposition efficiency within shorter time than Bu1 or Bu34.

| Time (day) | Bu1 PCP (μg/g, dry) | Bu1 Number of Bacteria (CFU/ml) | Bu1 + Bu34 PCP (μg/g, dry) | Bu1 + Bu34 Number of Bacteria (CFU/ml) | EBC100 PCP (μg/g, dry) | EBC100 Number of Bacteria (CFU/ml) |
|---|---|---|---|---|---|---|
| 0 | 1080 | $5.2 \times 10^8$ | 1080 | $1.4 \times 10^{11}$ | 1080 | $2.0 \times 10^8$ |
| 10 | 900 | $1.2 \times 10^{10}$ | 732 | $1.4 \times 10^{11}$ | 700 | $7.0 \times 10^{10}$ |
| 20 | 635 | $1.9 \times 10^{10}$ | 655 | $1.4 \times 10^{11}$ | 520 | $8.0 \times 10^{10}$ |
| 40 | 408 | $1.4 \times 10^{10}$ | 327 | $1.4 \times 10^{11}$ | 311 | $9.0 \times 10^{10}$ |
| 60 | 375 | $8.5 \times 10^{10}$ | 307 | $1.4 \times 10^{11}$ | 230 | $9.2 \times 10^{10}$ |
| 80 | 365 | $1.6 \times 10^{10}$ | 299 | $1.4 \times 10^{11}$ | 140 | $8.7 \times 10^{10}$ |
| 120 | 330 | $8.3 \times 10^9$ | 311 | $1.4 \times 10^{11}$ | 110 | $3.8 \times 10^9$ |
| 200 | 150 | $1.0 \times 10^{10}$ | 145 | $1.4 \times 10^{11}$ | 70 | $1.6 \times 10^9$ |

As understood from the above experimental examples, the novel bacterial consortium EBC1000 is useful for efficient decomposition of chlorine compounds as well as a high concentration of recalcitrant toxic chemicals contained in the wastewater to be dumped into the sea.

8. Analytical Test for Decomposition of Recalcitrant Wastewater [COD (Mn Method)] and Pentachlorophenol Compound by Means of the Individual Constituent of EBC1000

The individual pure isolated colonies of EBC100, EBC101, EBC103, EBC104, EBC105, EBC106, EBC107, EBC108 and EBC109 were inoculated into 20 ml of the liquid medium of waste acidic or alkaline wastewater (prepared by diluting 10% waste acid or alkaline wastewater containing 0.65 g of $K_2HPO_4$, 0.17 g of $KH_2PO_4$, 0.1 g of $MgSO_4$, 0.5 g of $NaNO_3$ and recalcitrant toxic chemicals of medical and petroleum industrial wastewater in 1 liter of deionized water, pH 0 to 14) and then to 20 ml of the liquid medium of chlorine compound (prepared by dissolving 0.65 g of $K_2HPO_4$, 0.17 g of $KH_2PO_4$, 0.1 g of $MgSO_4$, 0.5 g of $NaNO_3$ and 50 ppm of pentachlorophenol in 1 liter of deionized water, pH 7.2). After more than 10 days of shaking culture at 20 to 30° C., the COD and the PCP concentration were measured. As a result, the COD and the PCP concentration were decreased by, on average, 85% for EBC100, 67% for EBC101 and EBC103, 50 to 55% for EBC106, EBC107 and EBC108, and about 20% for EBC104, EBC105 and EBC109. This result showed that the individual constituent strains of the bacterial consortium EBC1000 have the ability to decompose the recalcitrant toxic chemicals and chlorine compounds. However, the bacterial consortium EBC1000 showed higher growth and decomposition efficiency than the individual constituent strains.

As described above, the novel bacterial consortium EBC1000 has the ability to rapidly decompose a high concentration of recalcitrant chemicals contained in the industrial wastewater and noxious waster materials to be dumped into the sea and purify soil, timber, seepage water and ground water contaminated by chlorine compounds, thus preventing and recovering excellently environmental pollutions.

Further, the bacterial consortium EBC1000 is useful for treating a high concentration of recalcitrant waste materials to be dumped into the sea, or soil, timber, seepage water and ground water contaminated by chlorine compounds in a way of aeration, as well as recovering the contaminated timber. Also, the present invention provides a mixture of Pseudomonas Bu34 strain (Korean Patent No. 154295) and genus Klebsiella Bu1 strain (Korean Patent Application No. 98-20706) used for recovery of contaminated timber or soil.

What is claimed is:

1. An isolated bacterial consortium EBC1000 (KCTC 0652 BP) which grows under culture in a Luria-Bertani nutrient medium at pH 5 to 8, at a temperature of 25 to 35° C. with shaking at 50 to 100 rpm/min for 24 to 48 hours, the Luria-Bertani nutrient medium containing 10 g of bacto-tryptone, 5 g of bacto-yeast extract and 10 g of NaCl in 1 liter of deionized water, wherein the bacterial consortium EBC1000 grows in a successive transfer culture under the same conditions.

2. A method for removing biologically recalcitrant chemicals from wastewater containing said biologically recalcitrant chemicals, comprising contacting the wastewater with an isolated bacterial consortium EBC1000, wherein the wastewater contains waste acidic or alkaline recalcitrant toxic chemicals contained in medical or petroleum industrial wastewater to be dumped into the sea, or chlorine compounds, wherein the recalcitrant toxic chemicals in the medical industrial wastewater comprise isopropyl alcohol, methylene chloride, NaOH, $Na_2SO_4$, dimethylamine and methanol, the recalcitrant toxic chemicals contained in the petroleum industrial wastewater comprise sodium hydrosulfite [$(NaSO_2)_2$], butadiene, sodium alkylaryl naphthalene sulfonate, acrylonitrile, tetra sodium ethylene diamine tetra acetate dihydrate, ferrous sulfate heptahydrate, tert-dodecyl mercaptan, para-methane hydroperoxide, N-diethyl hydroxyl amine and $CH_3CN$, and chlorine compounds comprise pentachlorophenol (PCP).

3. The isolated bacterial consortium EBC1000 as claimed in claim 1, comprising EBC100 being a strain of the genus Klebsiella.

4. The isolated bacterial consortium EBC1000 as claimed in claim 1, comprising EBC101 being a strain of the genus Klebsiella.

5. The isolated bacterial consortium EBC1000 as claimed in claim 1, comprising EBC103 being a strain of the genus Klebsiella.

6. The isolated bacterial consortium EBC1000 as claimed in claim 1, comprising EBC104 being a strain of the genus Escherichia.

7. The isolated bacterial consortium EBC1000 as claimed in claim 1, comprising EBC105 being a strain of the genus Providencia.

8. The isolated bacterial consortium EBC1000 as claimed in claim 1, comprising EBC109 being a strain of the genus Escherichia.

9. The method as claimed in claim 2, wherein the bacterial consortium EBC1000 comprises EBC100 being a strain of the genus Klebsiella.

10. The method as claimed in claim 2, wherein the bacterial consortium EBC1000 comprises EBC101 being a strain of the genus Klebsiella.

11. The method as claimed in claim 2, wherein the bacterial consortium EBC1000 comprises EBC103 being a strain of the genus Klebsiella.

12. The method as claimed in claim 2, wherein the bacterial consortium EBC1000 comprises EBC104 being a strain of the genus Escherichia.

13. The method as claimed in claim 2, wherein the bacterial consortium EBC1000 comprises EBC105 being a strain of the genus Providencia.

14. The method as claimed in claim 2, wherein the bacterial consortium EBC1000 comprises EBC109 being a strain of the genus Escherichia.

* * * * *

UNITED STATES PATENT AND TRADEMARK OFFICE
CERTIFICATE OF CORRECTION

PATENT NO.    : 6,383,797 B1
DATED         : May 7, 2002
INVENTOR(S)   : Sung-gie Lee It is certified that error appears in the above-identified patent and that said Letters Patent is hereby corrected as shown below:

<u>Title page,</u>
Item [22], PCT Filed, delete "July 22, 2000" and insert therefor -- July 11, 2000 --.

Signed and Sealed this

Twenty-fifth Day of March, 2003

JAMES E. ROGAN
*Director of the United States Patent and Trademark Office*